United States Patent [19]

Krämer et al.

[11] 4,000,299
[45] Dec. 28, 1976

[54] 1-(IMIDAZOL-1-YL)-1-[4-(4-CHLORO-PHENYL)PHENOXY]-3,3-DIMETHYLBUTAN-2-ONE, ITS SALTS AND A PROCESS FOR THEIR USE

[75] Inventors: Wolfgang Krämer; Karl Heinz Buchel; Manfred Plempel, all of Wuppertal, Germany

[73] Assignee: Bayer Aktiengesellschaft, Germany

[22] Filed: May 27, 1975

[21] Appl. No.: 580,718

[30] Foreign Application Priority Data

June 20, 1974 Germany .................. 2429514

[52] U.S. Cl. .................. 424/273; 260/309
[51] Int. Cl.$^2$ .................. C07D 233/60
[58] Field of Search .................. 260/309; 424/273

[56] References Cited

UNITED STATES PATENTS 3,812,142  5/1974  Meiser et al. .................. 260/309

FOREIGN PATENTS OR APPLICATIONS 2,105,490  8/1972  Germany .................. 260/309

Primary Examiner—Natalie Trousof

[57] ABSTRACT 1-(Imidazol-1-yl)-1-[4-(4-chlorophenyl)phenoxy]-3,3-dimethylbutan-2-one possesses antimicrobial activity, in particular antimycotic activity. The compound is prepared through the condensation of imidazole with 1-chloro-1-[4-(4-chlorophenyl)phenoxy]-3,3-dimethylbutan-2-one.

10 Claims, No Drawings

1-(IMIDAZOL-1-YL)-1-[4-(4-CHLOROPHENYL)-PHENOXY]-3,3-DIMETHYLBUTAN-2-ONE, ITS SALTS AND A PROCESS FOR THEIR USE

DETAILED DESCRIPTION

The present invention relates to 1-(imidazol-1-yl)-1-[4-(4-chlorophenyl)phenoxy]-3,3-dimethylbutan-2-one and its salts, to a process for their preparation and to their antimicrobial use.

It is known that some N-tritylimidazoles exhibit an antimycotic effect; see e.g., Belgian patent specification No. 720,801. Antimycotically active imidazolyl-(1)-etherketones have also already been disclosed; see e.g., German Offenlegungsschrift No. 2,105,490 and Belgian Pat. No. 804,092. However, these compounds are not always satisfactory particularly when administered orally at very low doses. Furthermore their antimycotic spectrum is not very broad.

The present invention provides an imidazol-1-yl-ether-ketone of the formula:

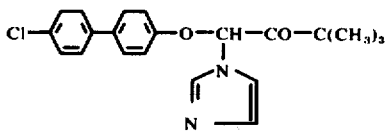

(I)

and to its pharmaceutically acceptable salts.

The compounds of the invention exhibit powerful antimycotic effects.

The compounds of the invention may be prepared by reacting a compound of the formula:

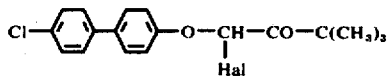

(II)

in which Hal is a halogen atom, preferably chlorine or bromine, with imidazole in the presence of an acid binding agent, and, optionally converting the resulting base into a salt. The interconversion of the compound of Formula 1 and its salts is accomplished by conventional techniques.

Surprisingly, the imidazol-1-yl-ether-ketone according to the invention, and its salts, exhibit a substantially greater antimycotic effect, particularly on oral administration, and also on parenteral administration and local application, than known antimycotic imidazole derivatives and known and commercially available products such as, for example, griseofulvin, tolnaftate and nystatin.

1-Chloro-1-[4-(4-chlorophenyl)phenoxy]-3,3-dimethylbutan-1-one and imidazole are employed as starting materials and the course of the reaction can be represented by the following equation:

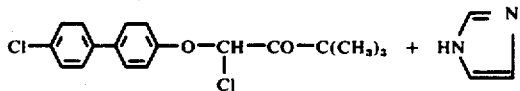

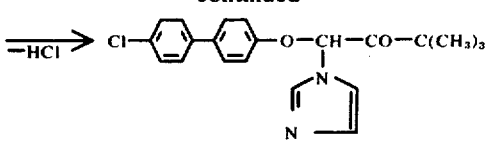

The above halogen compound of Formula II has not previously been disclosed but can be prepared according to known processes. For example, 4-(4-chlorophenyl)phenol is reacted with a haloketone of the formula:

$$Hal-CH_2-CO-C(CH_3)_3 \qquad (III)$$

in which Hal has the above-mentioned meaning to yield 1-[4-(4-chlorophenyl)phenoxy]-3,3-dimethylbutan-2-one in which the active hydrogen atom is then replaced by halogen through conventional halogenation techniques.

Preferred diluents used in the preparation of the compound of the invention are polar organic solvents, as for example nitriles such as acetonitrile, sulfoxides such as dimethylsulfoxide, formamides such as dimethylformamide, ketones such as acetone, ethers such as diethyl ether and tetrahydrofuran, nitroalkanes such as nitromethane and unsymmetrical chlorohydrocarbons such as methylene chloride and chloroform. The reaction is carried out in the presence of an acid binding agent, preferably an excess of imidazole but any other organic acid binding agents such as lower tertiary alkylamines or aralkylamines, as for example triethylamine or dimethylbenzylamine, also can be employed. The reaction temperature can be varied within a substantial range, generally from about 20° to about 150° C, preferably from about 80° to about 120° C. About 1 mol of imidazole and about 1 mold of acid binding agent are employed per 1 mol of the compound of Formula II. The final compound can be isolated via conventional techniques. The solvent is thus evaporated in vacuo and the residue is taken up in a polar organic solvent. This is followed by an extraction with water to remove the imidazole hydrochloride also produced, and by evaporation of the solution to dryness. The free base is further purified by recrystallization while the salt is formed by treatment with an appropriate acid.

The preferred salts of the imidazol-1-yl-ether-ketone of Formula 1 are those of physiologically tolerable acids. Examples of such acids are the hydrogen halide acids, especially hydrochloric acid, phosphorus acids, sulphuric acid, nitric acid, monofunctional and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and 1,5-naphthalenedisulphonic acid.

The new compound of Formula I and its salts exhibit very powerful antimicrobial effects. They display a broad spectrum of action, for example against dermatophytes and yeasts and also against biphase fungi and moulds, as well as against staphylococci and trichomonades, and can thus be successfully employed in combatting fungal infections in man and animals, such as dermatomycoses and systemic mycoses caused by *Trichophyton mentagrophytes* and other species of *Trichophyton*, species of *Microsporon*, *Epidermophyton*

*floccosum, blastomycetes* and biphase fungi as well as moulds.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

In general it has proved advantageous to administer amounts of from about 10 mg to about 300, preferably from 50 to 200, mg/kg of body weight per day to achieve effective results. Nevertheless, it is at times necessary to deviate from these dosage rates, and in particular to do so as a function of the nature and body weight of the human or animal subject being treated, the individual's response, the formulation, the stage of the disease, and the interval at which it is administered. Thus in some cases, it suffices to use less than the above-mentioned minimum dosage while in other cases the upper limit must be exceeded to achieve the desired results. Where larger amounts are administered it is often desirable to divide these into several individual administrations over the course of the day.

The microbiological activity of the active compounds usable according to the invention can be conveniently observed in vitro and in vivo models. As will be seen from these data, the compounds are well-tolerated and very effective antimycotics having a broad spectrum of action on oral, parenteral and local administration. They are superior to clotrimazol, miconazol and all other azole derivatives by virtue of their effectiveness at very low doses on oral administration, superior to griseofulvin, tolnaftate, nystatin and pimaricin by virtue of their very much broader spectrum of action, and superior to amphotericin B by virtue of their substantially lower toxicity.

1. in vitro activity.

The preparations according to the invention show a broad activity, in vitro, against fungi which are pathogenic to humans and animals, Gram positive bacteria and trichomonades. The table which follows lists MIC values of the preparations in comparison with representative species of fungi, *Staph. aureus* and *Trichomonas vaginalis*.

The activity was tested in the series dilution test on Sabouraud's milieu d'epreuve, meat broth-glucose, bouillon, Francis blood agar and Kimmig malt extract-peptone medium. The incubation temperatures were 28° and 37° C and the incubation time was 24, 48 and 96 hours. The inoculum was in every case 5 × $10^3$ germs/ml of substrate. The results are summarized in Table A and compared with two commercially available preparations while the effects of some previously known imidazol-1-yl-ether derivatives are shown in Table B.

Table A in vitro activity
MIC values in γ/ml of nutrient medium for the case of

| Species of germ | Cl-C6H4-C6H4-O-CH(imidazolyl)-CO-C(CH3)3 | Cl-C6H4-C6H4-O-CH(imidazolyl)-CO-C(CH3)3 × HCl | Griseo-fulvin | Nystatin |
|---|---|---|---|---|
| Trich. ment. | <1 | <1 | 5–10 | 20 |
| Microsporon canis | <1 | <1 | 5–10 | 20–40 |
| Candida albicans | 2–4 | 2 | >100 | 5 |
| Torulopsis glab. | 2 | 2 | >100 | 5 |
| Cryptococcus neof. | 1–2 | 1–2 | >100 | 4–10 |
| Aspergillus spec. | <1 | <1 | 40–100 | 40–100 |
| Sporothrix Schenckii | 0.1 | 0.5 | >100 | 40 |
| Coccidioides immitis | 0.1 | 0.1 | >100 | 40 |
| Pityrosporum ovale | <1 | <1 | >100 | ? |
| Staph. aureus | 8 | 4 | >100 | >100 |
| Trichomonas vaginalis | 250 | 250 | >1,000 | >1,000 |

Table B in vitro activity of known imidazolyl-(1)-ether derivatives
MIC values in γ/ml of nutrient medium for the case of

| Compound | Trichophyton ment. | Candida albicans | Microsporon felinum | Aspergillus spec. |
|---|---|---|---|---|
| 2,6-dichlorophenyl-O-CH(imidazolyl)-CO-C6H5 | 4 | 4 | 40 | 100 |
| 3-chlorophenyl-O-CH(imidazolyl)-C(OH)2-C6H5 × HCl | 4 | 4 | 40 | 40 |
| 4-chlorophenyl-O-C(imidazolyl)(C6H5)-CO-C6H5 | 10 | 10 | 40 | 10 |
| 3-chlorophenyl-O-CH(imidazolyl)-CO-C6H5 | 4 | 10 | 40 | 40 |
| 4-chlorophenyl-O-CH(CH2-imidazolyl)-CO-C(CH3)3 | 4 | 4 | — | 8 |
| 4-bromophenyl-O-CH(CH2-imidazolyl)-CO-C(CH3)3 × HCl | 8 | 4 | — | 4 |

Table B-continued in vitro activity of known imidazolyl-(1)-ether derivatives

| Compound | MIC values in γ/ml of nutrient medium for the case of | | | |
|---|---|---|---|---|
| | Trichophyton ment. | Candida albicans | Microsporon felinum | Aspergillus spec. |
| ⌬-O—CH—CO—C(CH₃)₃ / CH₂ / N⌬N  × HCl (2-phenylphenyl derivative) | 8 | 4 | — | 8 |
| F-⌬-O—CH—CO—C(CH₃)₃ / CH₂ / N⌬N | 8 | 4 | — | 4 |

The antimycotic type of effect is primarily fungistatic; a fungicidal action, with a reduction of the inoculum by more than 99%, is achievable with 2 to 4 times the minimum inhibitory concentrations in vitro and in vivo.

Development of resistance of initially sensitive germs could not be found by the passage method and by the Szibalsky technique. This makes it possible to state that development of resistance, if it occurs at all, takes place slowly and in accordance with the multiple-step scheme.

2. in vivo activity.

The preparations claimed also have a curative effect in vivo in the case of dermatophytoses and systemic mycoses when administered orally or parenterally or applied locally to the infected test animal.

a. Effect on oral administration.

I. on candidosis in mice.

White mice of the $CF_1SPF$ strain are infected with $1-3 \times 10^6$ Candida albicans cells intravenously by puncture of the tail vein. Untreated control animals die from the 3rd to the 6th day after infection as a result of the candidosis of the organs which develops. If the preparations claimed are given orally in doses of $2 \times 6.25 - 2 \times 150$ mg/kg of body weight, starting from the day of infection and up to the 5th day after infection, the following survival rates are observed:

The previously known imidazol-1-yl-ether derivatives in Table B show, at a dose of 50 mg/kg of body weight to 125 mg/kg of body weight, given twice daily, survival rates of approximately 75% to 85% on the 6th day after infection.

II. On trichophytosis in mice and guinea pigs, caused by Trich. mentagrophytes and Trich. Quinckeanum:

Mice ($CF_1SPF$) and guinea pigs (Pearl bright white) are infected on the back with suspensions of spores of Trich. ment. or Trich. Quinckeanum. In the case of the untreated control animals, the symptoms of a dermatophytosis, typical of the pathogen, developed within 12 days after infection.

Oral doses of $1 \times 25$ to $1 \times 100$ mg/kg of body weight administered from the 3rd to the 12th day after infection entirely suppress the development of the experimental dermatophytoses.

b. Effect of local application, on trichophytosis in guinea pigs.

White guinea pigs weighing 400–500 g are infected on the back with a suspension of spores of Trich. ment. in the usual form. For local therapy, the compounds in a 1% solution in polyethylene glycol 400 are applied as a thin layer to the infected area, once daily, from the 4th to the 13th day after infection, and rubbed in lightly with a horn spatula. Table D which follows shows the curative effects of the preparations in comparison to the untreated control:

Table C

Effect on oral administration, for the model of experimental candidosis in mice
Survival rates on the 6th day after infection, in %, for the case of

| Dose in mg/kg of body weight | Cl-⌬-⌬-O—CH—CO—C(CH₃)₃ / N⌬N | Cl-⌬-⌬-O—CH—CO—C(CH₃)₃ / N⌬N × HCl | Nystatin |
|---|---|---|---|
| 2 × 6.25 | 55 | 95 | <10 |
| 2 × 12.5 | 70 | 95 | <10 |
| 2 × 25 | 80 | 100 | <10 |
| 2 × 50 | 100 | 100 | <10 |
| 2 × 100 | 100 | 100 | 30 |
| 2 × 150 | 100 | 100 | 50 |
| Controls | average 3 – 5% | | |

Table D

Effect on local administration, for the model of experimental Trichophytosis in guinea pigs.

| Preparation | Intensity of the curative effect on local administration on the 13th day after infection |
|---|---|
| 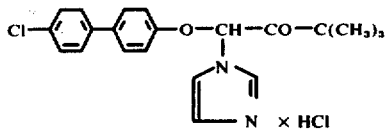 | +++ |
| (second structure with × HCl) | ++++ |
| Control | Severe dermatophytosis |

+++ = good effect, that is to say only slight signs of infection
++++ = very good effect, that is to say no detectable symptoms of infection.

c. Guideline data on the pharmacokinetics after oral administration.

The preparations claimed are resorbed well on oral administration to mice and guinea pigs and after doses of 50 mg/kg of body weight give serum peak concentrations of 4–6 γ/ml for the case of the hydrochloride.

The elimination half-life is approximately 4.5–5.5 hours; approximately 20% of the elimination takes place renally and ~70% faecally via the bile.

d. Acute toxicity and toleration.

On oral administration to mice, rats and guinea pigs, the preparations mentioned showed an $LD_{50}$ of between 750 and 1,200 mg/kg of body weight. The toleration by skin, on local application of 1% strength solutions, was excellent.

EXAMPLE 1

605 g (2 mols) of 1-[4-(4-chlorophenyl)phenoxy]-3,3-dimethylbutan-2-one were dissolved in 3 l of methylene chloride. 170 ml (2.1 mols) of sulphuryl chloride were added dropwise at 40° C over the course of 2 to 3 hours and the mixture was then stirred for 15 hours at the same temperature. Thereafter the solvent was distilled off in vacuo and the residue was dissolved in 1.5 l of methyl ethyl ketone. This solution was added dropwise, with slight cooling at 20° C, to a suspension of 280 g (4 mols) of imidazole and 280 g (2 mols) of powdered potassium carbonate in 3 l of methyl ethyl ketone. After stirring for 48 hours at room temperature, the solvent was distilled off. The residue was taken up in 3 l of methylene chloride, the solution was washed with four times 1 litre of water and then dried over sodium sulphate and the solvent was distilled off in vacuo. The oil which remained was recrystallized from 1 litre of diisopropyl ether.

This crude base was dissolved in approx. 1.2 l of methylene chloride. 550 ml of an approx. 4 N solution of hydrochloric acid in ether were added cautiously and thereafter the solvent was distilled off. 1 litre of ethyl acetate was added to the oil which remained and the mixture was heated, whereupon spontaneous crystallization occurred. After heating for one-half hour, the product was filtered off hot, washed with a little ethyl acetate and dried in vacuo. After twice recrystallizing from acetone, 210 g (26% of theory) of 1-(imidazol-1-yl)-1-[4-(4-chlorophenyl)phenoxy]-3,3dimethyl-butan-2-one hydrochloride of melting point 148°–150° C were obtained.

Starting material

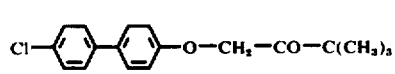

280 g (2 mols) of powdered potassium carbonate were suspended in 2 l of methyl ethyl ketone. 409 g (2 mols) of 4'-chlorohydroxybiphenyl were added and the mixture was heated to the boil. Thereafter 269 g (2 mols) of α-chloropinacolone were added dropwise over the course of 1 hour and the mixture was heated for 15 hours under reflux. After cooling, the solid residue was filtered off, washed and recrystallized from ligroin. 513 g (79% of theory) of 1-[4-(4-chlorophenyl)phenoxy]-3,3-dimethylbutan-2-one of melting point 90° C were obtained.

EXAMPLE 2

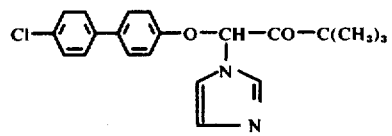

The free base from Example 1 was obtained in accordance with the method described there by repeatedly recrystallizing the crude base from diisopropyl ether. The melting point was 98°–100° C.

Table E

| Example No. | The following were prepared analogously: Structure | Melting point |
|---|---|---|
| 3 | 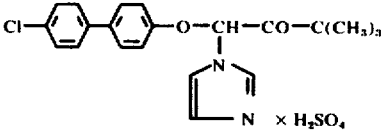 × H$_2$SO$_4$ | 135° C |
| 4 | × HNO$_3$ | 120° decomposition |
| 5 | × 2H$_3$PO$_4$ | 150° C |
| 6 | × COOH–COOH | 106° C |
| 7 | 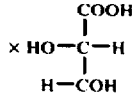 | 78° decomposition |
| 8 | 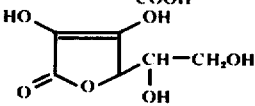 | 81° C |

What is claimed is:

1. A compound selected from the group consisting of 1-(imidazol-1-yl)-1-[4-(4-chlorophenyl)phenoxy]-3,3-dimethylbutan-2-one and the pharmaceutically acceptable nontoxic acid addition salts thereof.

2. The compound according to claim 1 which is 1-(imidazol-1-yl)-1-[4-(4-chlorophenyl)phenoxy]-3,3-dimethylbutan-2-one.

3. A compound according to claim 1 which is the salt of said 1-(imidazol-1-yl)-1- [4-(4-chlorophenyl)-phenoxy]-3,3-dimethylbutan-2-one with a hydrogen halide acid, phosphoric acid, sulfuric acid, nitric acid, a sulfonic acid, a monobasic carboxylic acid or a dibasic carboxylic acid.

4. The compound of claim 1 which is 1-(imidazol-1-yl)-1-[4-(4-chlorophenyl)phenoxy]-3,3-dimethylbutan-2-one hydrochloride.

5. The compound of claim 1 which is 1-(imidazol-1-yl)-1-[4-(4-chlorophenyl)phenoxy]-3,3-dimethylbutan-2-one nitrate.

6. The compound of claim 1 which is 1-(imidazol-1-yl)-1-[4-(4-chlorophenyl)phenoxy]-3,3-dimethylbutan-2-one phosphate.

7. The compound of claim 1 which is 1-(imidazol-1-yl)-1-[4-(4-chlorophenyl)phenoxy]-3,3-dimethylbutan-2-one sulfate.

8. The compound of claim 1 which is 1-(imidazol-1-yl)-1-[4-(4-chlorophenyl)phenoxy]-3,3-dimethylbutan-2-one oxalate.

9. The method of combatting microbial infections in humans and animals which comprises administering to said human or animal an antimicrobially effective amount of a compound according to claim 1.

10. A pharmaceutical composition comprising an antimicrobially effective amount of a compound according to claim 1 in combination with a pharmaceutical carrier or diluent.

* * * * *